United States Patent
Kawahara

(10) Patent No.: US 6,835,859 B2
(45) Date of Patent: Dec. 28, 2004

(54) METHOD FOR CONTINUOUSLY PRODUCING 3,3',5,5'-TETRA-T-BUTYL-4,4'-BIPHENOL

(75) Inventor: Mikio Kawahara, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/684,638

(22) Filed: Oct. 14, 2003

(65) Prior Publication Data

US 2004/0122263 A1 Jun. 24, 2004

(30) Foreign Application Priority Data

Nov. 1, 2002 (JP) ......................................... 2002-319589

(51) Int. Cl.$^7$ ............................................... C07L 39/12
(52) U.S. Cl. ....................................................... 568/730
(58) Field of Search ......................................... 568/730

(56) References Cited

U.S. PATENT DOCUMENTS 4,238,627 A  12/1980  Reichle 6,689,921 B2 * 2/2004 Kaplan ........................ 568/730

FOREIGN PATENT DOCUMENTS

| JP | 04-60457 | 9/1992 |
| JP | 06-74227 | 9/1994 |

* cited by examiner

Primary Examiner—Michael L. Shippen
(74) Attorney, Agent, or Firm—Knobbe, Martens, Olson & Bear LLP

(57) ABSTRACT

A method for continuously producing 3,3',5,5'-tetra-t-butyl-4,4'-biphenol by oxidizing/dimerizing 2,6-di-t-butylphenol, comprising the steps of: supplying 2,6-di-t-butylphenol to a first reaction section of a reaction apparatus in which at least the first reaction section and a second reaction section are connected in series; supplying alkali catalyst to at least said first reaction section; and distributing oxygen containing gas to each reaction section respectively; whereby a reaction mixture containing 3,3',5,5'-tetra-t-butyl-4,4'-biphenol is obtained from a last reaction section.

13 Claims, 3 Drawing Sheets

METHOD FOR CONTINUOUSLY PRODUCING 3,3',5,5'-TETRA-T-BUTYL-4,4'-BIPHENOL

BACKGROUND OF THE INVENTION

1. Field of the Invention

This invention relates to a method for continuously producing 3,3',5,5'-tetra-t-butyl-4,4'-biphenol, more specifically to a method for continuously producing 3,3',5,5'-tetra-t-butyl-4,4'-biphenol, an intermediate product of industrially important 4,4'-biphenol as the raw material of thermostable engineering plastic at a high invert ratio by restricting the production of byproducts.

2. Description of the Related Art

A method for producing 3,3',5,5'-tetra-t-butyl-4,4'-biphenol (hereinafter TBBP) having 2,6-di-t-butylphenol (hereinafter 26B) as raw material that is oxidized with oxygen containing gas under a presence of alkali catalyst has already been known. For example, one of the known methods produces 3,3',5,5'-tetra-t-butyl-4,4'-diphenoquinone (hereinafter TBBPQ) by oxidizing/dimerizing 26B under the presence of alkali catalyst, then reducing or carrying out proton disproportionate reaction to form TBBP (see Japanese Patent Publication No. Hei 4-60457). Further, a method for producing TBBP with one step by oxidizing/coupling 26B (see Japanese Patent Publication No. Hei 6-74227) is also known. TBBP obtained by the above-mentioned methods is formed into 4,4'-biphenol by removing butyl therefrom.

Formula 1

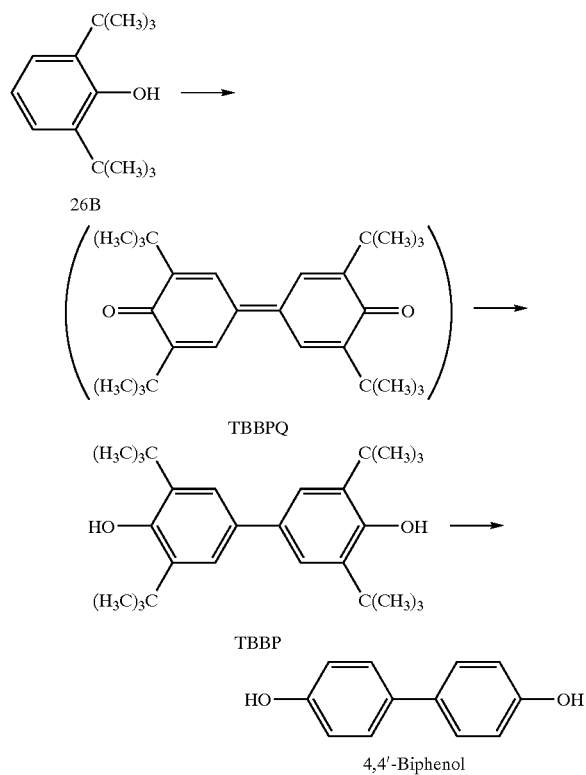

However, these known conventional methods for producing TBBP are the batch-type production method using a single reactor. Such batch-type production method may suit for a small size of TBBP production. However, for a mass production, the reaction vessel may need to be enlarged or plural reaction vessels have to be aligned by which the batch process is performed. In either case, it is associated with a disadvantage of poor cost efficiency and poor productivity.

Further, when 26B as the raw material is oxidized with oxygen containing gas under the presence of alkali catalyst, TBBP is mainly produced. Simultaneously, as by-product, diphenoquinone such as TBBPQ is also produced. If this reaction is carried out with a continuous reaction method, conversion ratio of 26B is reduced compared with the reaction by means of the batch type. Then, if the conversion ratio of 26B is increased up to the same level as that of the batch type, it creates a problem of byproduct, particularly, diphenoquinone such as TBBPQ causing discoloration to the obtained products.

SUMMARY OF THE INVENTION

Recently, there has been a high demand for the development of a method for continuously producing TBBP, that is an intermediate product of industrially important 4,4'-biphenol as the raw material of thermostable engineering plastic at a high invert ratio by restricting the production of byproducts. It is an object of the present invention to provide a method for continuously producing TBBP at a high selection ratio by restricting the product of byproducts by using and oxidizing/dimerizing the raw material 26B.

The present invention provides a method for continuously producing 3,3',5,5'-tetra-t-butyl-4,4'-biphenol by oxidizing/dimerizing 2,6-di-t-butylphenol, comprising steps of supplying 2,6-di-t-butylphenol to a first reaction section of a reaction apparatus in which at least the first and second reaction sections are connected in series; supplying alkali catalyst to at last said first reaction section; distributing oxygen containing gas to each reaction section respectively; whereby a reaction mixture containing 3,3',5,5'-tetra-t-butyl-4,4'-biphenol is obtained from the last reaction section.

Explanation of symbols used is as follows: 1: first reaction section (first reaction vessel); 2: second reaction section (second reaction vessel); 3: distribution pipe; 4: raw material supply pipe; 5: air supply pipe; 6: alkali catalyst supply pipe; 7: distribution pipe; 8: distribution pipe; 9: cooler; 10: distribution pipe; 11: reaction tower; 12: board with holes; 13: first reaction section (upper part of the reaction tower); 14: second reaction section (lower part of the reaction tower); 15: raw material supply pipe; 16: air supply pipe; 17: alkali catalyst supply pipe; 18: distribution pipe; 19: distribution pipe; 20: cooler; 21, 21a: board with holes; 22: first reaction section; 23: second reaction section; 24: third reaction section; 25: first step reaction area; 26: latter step reaction area; 30: water; 31: waste gas.

DETAILED DESCRIPTION OF THE PREFERRED EMBODIMENT

The present invention employs a reaction apparatus in which at least first and second reaction sections are connected in series. According to the present invention, as long as the first and second reaction sections are connected in series, each reaction section does not have to be formed by the independent reactors. Therefore, the reaction apparatus may be formed by dividing an interior of a single reactor into plural sections.

Figure 1:
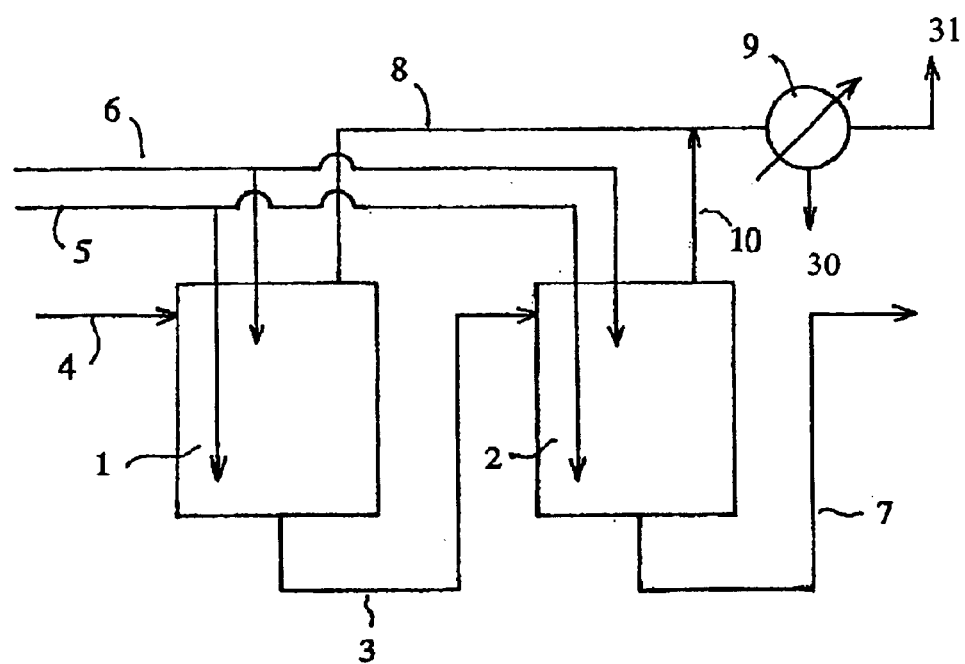
FIG. 1 is a diagram showing one example of the reaction apparatus described in the present invention.

The present invention is specifically explained in reference to the attached drawings. FIG. 1 shows one example of the reaction apparatus that embodies the method of the present invention. This reaction apparatus comprises independently a first reaction vessel 1 and a second reaction vessel 2, wherein both of them are defined to be the first and second reaction sections, respectively. The first reaction vessel 1 is connected to the second reaction vessel 2 in series by a distribution pipe 3.

The raw material 26B is continuously supplied from a raw material supply pipe 4 to the first reaction vessel 1 (the first reaction section). Alkali catalyst is supplied to at least first reaction vessel by means of an alkali catalyst supply pipe 6. On the other hand, oxygen containing gas is continuously supplied to each of the first reaction vessel 1 and the second reaction vessel 2 (the second reaction section). Namely, according to the present invention, the alkali catalyst may be continuously supplied only to the first reaction section. It is also acceptable that the alkali catalyst is separately supplied to each of the first and second reaction sections. However, the latter is more preferable.

Reaction mixture obtained in the first reaction vessel 1 is sent to the second reaction vessel 2 via the distribution pipe 3, whereby the reaction continues in the second reaction vessel. Reaction mixture obtained in the second reaction vessel is guided to the outside via a distribution pipe 7. Waste gas containing water generated in the first reaction vessel is led to a cooler 9 through a distribution pipe 8 wherein the water 30 is removed from the waste gas by means of vapor-liquid separation. The remaining waste gas 31 is discharged to the outside. Waste gas containing water generated in the second reaction vessel is led to the cooler 9 through a distribution pipe 10, wherein the water is removed from the waste gas by means of the vapor-liquid separation. The remaining waste gas is then discharged to the outside.

When the reaction is carried out by utilizing the reaction apparatus as shown in FIG. 1, according to the present invention, it is preferable that reaction temperature in the second reaction vessel, i.e., the latter step, is higher than that in the first reaction vessel, i.e., the first step.

Figure 2:
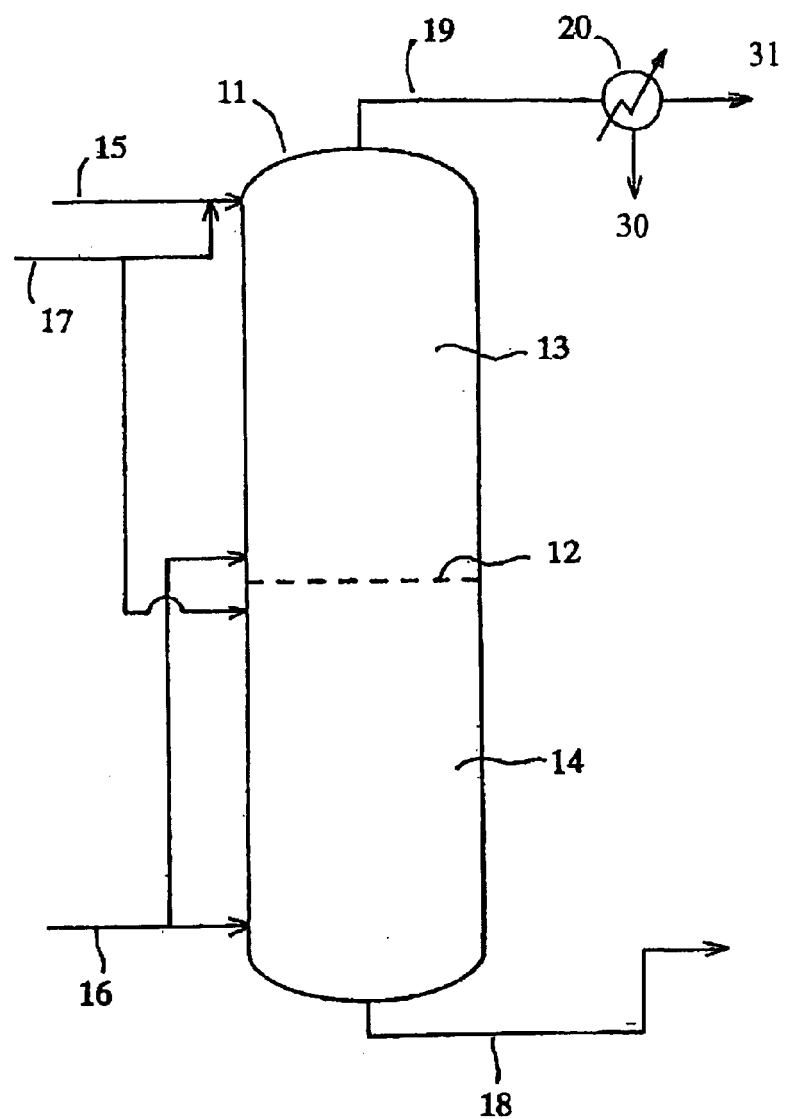
FIG. 2 is a diagram showing another example of the reaction apparatus described in the present invention.

FIG. 2 shows another example of the reaction apparatus in the present invention. This reaction apparatus includes a single reaction tower 11 divided by a board 12 having plural holes, wherein an upper section of the tower is defined to be a first reaction section 13 and a lower section is defined to be a second reaction section 14. In this reaction apparatus, the raw material 26B is supplied from a raw material supply pipe 15 to the first reaction section 13, preferably to the upper part of the tower. Oxygen containing gas is supplied to the first and second reaction sections by an air supply pipe 16, preferably to a lower part of each reaction section separately. Similarly, alkali catalyst is continuously supplied to the first reaction section (and the second reaction section, preferably to the upper part of each reaction section respectively) by an alkali catalyst supply pipe 17.

According to the present invention, the raw material 26B as liquid dissolved in the solvent is preferably supplied to the inside of the tower from the upper part of the reaction tower. Further, the alkali catalyst is preferably supplied to the upper part of each reaction section as liquid. On the other hand, the air is supplied to the lower part of each reaction section. Thus, the liquid such as the raw material 26B and alkali catalyst, and the oxygen containing gas advance along the inside of the reaction tower, whereby the vapor-liquid contact facilitates the reaction process.

According to the present invention, when the reaction is carried out by using the reaction apparatus of FIG. 2, the reaction temperature in the second reaction vessel, i.e., the latter step is preferably higher than the reaction temperature in the first reaction vessel, i.e., the first step.

Figure 3:
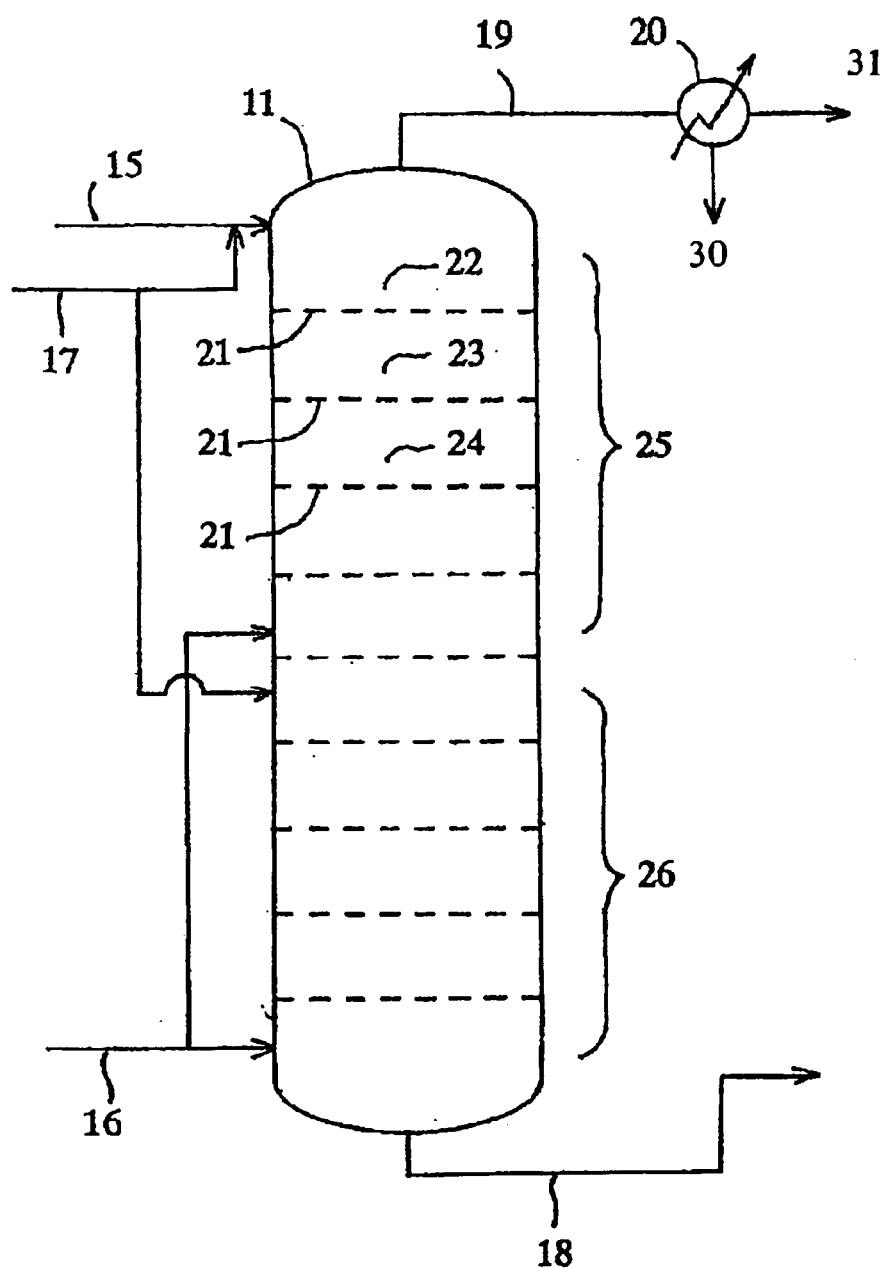
FIG. 3 is a diagram showing further another example of the reaction apparatus described in the present invention.

Further another example of the present invention employs the reaction tower having plural reaction sections as the reaction apparatus shown in FIG. 3. In this reaction apparatus, the reaction tower 11 is divided by plural boards 21 having plural holes to form a first reaction section 22 on the top of the tower, followed by the second reaction section 23, the third reaction section 24 and so forth. Unlike the aforementioned reaction apparatus, it has three or more reaction sections. The shown reaction apparatus has ten reaction sections.

When using the reaction apparatus comprising the reaction tower having plural reaction sections, as mentioned above, the raw material 26B may be supplied to the first reaction section, while oxygen containing gas and alkali catalyst may be supplied to all reaction sections including the first reaction section. It is also possible that, as shown in the drawing, the first, second, third, fourth and fifth reaction sections are defined to be the first step reaction area 25, whereas the sixth, seventh, eight, ninth and tenth reaction sections are defined to be the latter step reaction area 26. This first step is regarded as the first reaction section, and the latter step is regarded as the second reaction section. As described in the foregoing, the raw material 26B may be supplied to the first reaction section 22 at the top of the tower via the raw material supply pipe 15. The oxygen containing gas may be distributed to the fifth and tenth reaction sections respectively via the air supply pipe 16. Further, the alkali catalyst may be supplied to the first and sixth reaction sections respectively via the alkali catalyst supply pipe 17.

According to the present invention, the reaction apparatus is employed in which at least first and second reaction sections are connected in series. In order to easily control the reaction process, and from economical reasons, the number of the reaction sections is preferably limited to two to five.

As mentioned above, when the reaction is carried out by using the reaction apparatus shown in FIGS. 1 and 2, it is preferable that the reaction temperature in the second reaction vessel, i.e., the latter step, is higher than the reaction temperature in the first reaction vessel, i.e., the first step. When the reaction is carried out with the reaction apparatus shown in FIG. 3, it is preferable that the plural reaction sections are appropriately divided to the first step reaction area and the latter step reaction area. It is preferable that the reaction temperature in the second reaction section is higher than the first reaction section. For example, with the use of the reaction apparatus in FIG. 3, as mentioned above, the first step reaction area 25 includes the first, second, third, fourth and fifth reaction sections, whereas the latter step reaction area 26 includes the sixth, seventh, eighth, ninth and tenth reaction sections. In this arrangement, it is preferable that the reaction temperature of the latter step reaction area is higher than that of the first step reaction area.

According to the method described in the present invention, the raw material 26B may be refined. For example, as described in Japanese Patent Publication No. Hei 6-74227, phenol and isobutylene are reacted under a presence of aluminum phenoxide, followed by a removal of aluminum phenoxide catalyst, whereby a solution containing crude 26B is obtained.

According to the present invention, as mentioned above, the raw material 26B is continuously supplied to the first reaction section of the reaction apparatus at a predetermined ratio as liquid. In this case, the liquid containing the raw material 26B is first preheated up to the reaction temperature by an appropriate means such as a heater before being supplied to the first reaction section of the reaction apparatus.

Furthermore, as the alkali catalyst for oxidizing/dimerizing reaction, alkali metallic hydroxide such as potassium hydroxide and sodium hydroxide are preferably used. Such alkali catalyst is normally used within a range of 0.1–2.0 weight %, more preferably 0.05–0.2 weight % relative to the raw material 26B to be used. The alkali catalyst is equally diffused to the reaction mixture and used as the solution with 2–30 weight %, preferably.

According to the present invention, such alkali catalyst may be continuously supplied to the first reaction section or distributed to first and second reaction sections and their subsequent reaction sections. When the alkali catalyst is distributed to the subsequent reaction sections, more than 50% of used alkali catalyst is preferably supplied to the first reaction section, whereas the remaining alkali catalyst is preferably supplied to the second and the other following reaction sections.

According to the present invention, as mentioned above, the raw material 26B and the alkali catalyst are supplied to the reaction apparatus as liquid. Oxidation reaction by means of the oxygen containing gas as the oxidizing agent is carried out in the liquid phase. As the reaction solvent, it does not matter whether or not an organic solvent is further used. If the organic solvent is used, any kind of solvent can be used as long as it is inert to the reaction and able to dissolve TBBP produced as a result of the reaction. As a few examples of such solvent, alkylphenol group such as 2-t-butylphenol, p-t-butylphenol, and 2,4,6-tri-t-butylphenol, alkyl-substituted or halogen-substituted aromatic hydrocarbon group such as mesitylene and chlorobenzene, or paraffin group such as decalin, may be selected. These solvents are used up to twofold weight relative to 26B, whenever necessary.

In the method described in the present invention, as the oxygen containing gas, for example, oxygen, mixed gas in which oxygen is diluted by inert gas such as nitrogen or air, may be used; however, the air is most commonly utilized. Such oxygen containing gas contains oxygen at 0.3–2.0 times, preferably 0.8–1.0 times of the theoretical amount for oxidizing/dimerizing.

According to the present invention, as mentioned above, the oxygen containing gas is continuously distributed to first and second reaction sections and other subsequent reaction sections. In this case, the oxygen containing gas may be equally supplied to the first and second reaction sections and other subsequent reaction sections. Preferably 55–85%, more preferably 60–80% of oxygen containing gas to be used is supplied to the first reaction section. Whereas the remaining volume of gas is supplied to the second and its subsequent reaction section in order to improve the selection ratio of the reaction and prevent byproducts.

When supplying the oxygen containing gas is supplied to a certain reaction section, its pressure (blowing pressure) is not particularly restricted. However, under gage pressure, it is within a range of 0–5 MPa, more preferably 0.1–0.5 MPa.

In the present invention, it depends on oxygen partial pressure though, the reaction temperature is normally within a range of 150–250° C., more preferably within a range of 170–200° C. The reaction temperature may be same in the first and latter step reaction areas. However, as mentioned above, it is preferable that the reaction temperature in the latter step reaction area is higher by 0–30° C. than that of the first step reaction area.

With the use of the reaction apparatus mentioned above, when the continuous oxidizing/dimerizing reaction of the raw material 26B is carried out under the above-described condition, it requires the reaction time of 2–16 hours, more preferably 4–10 hours, as a total residence time. The total residence time is a duration from the time when the raw material 26B starts supplying to the reaction apparatus until the time when the raw material is discharged from the last reaction section. The residence time in each reaction section can be same. It is also possible that the residence time in the second and the subsequent reaction sections may be shorter or longer than the first reaction section.

The present invention is described in reference to Examples and a Comparative Example in the following. It is regardless to say that the present invention is not limited to the following examples.

COMPARATIVE EXAMPLE 1

510 g of crude material 26B consisting of 80.8 weight % of the raw material 26B, 3.7 weight % of o-t-butylphenol 26B and 13.5 weight % of 2,4,6-tri-t-butylphenol, and 12.8 g of potassium hydroxide solution having 6 weight % were applied to an autoclave having a mixer, a thermostat and a pressure gage. After heated at 190° C., the pressure 0.3 MP (gage pressure) was applied with the air blown at 6.25 NL/hour, whereby the reaction was carried out for 8 hours. After the reaction, the obtained reaction mixture was analyzed by a gas chromatography. The result showed that TBBP within the reaction mixture was 63.2 weight % and the raw material 26B was 14.6 weight %. The selection ratio relative to 26B in the crude raw material 26B was 96.0%. In addition, Gardener dissolution color of 20 weight % of toluene solution in the reaction mixture was 16.

It should be noted that the section ratio is defined to be [2×(the mol number of TBBP produced in the reaction/the mol number of 26B consumed in the reaction)×100 (hereinafter same).

EXAMPLE 1

Two autoclaves having a mixer, a thermostat and a pressure gage were arranged in series, and a series of devices as shown in FIG. 1 was assembled to which a reaction mixture including 33 weight % of TBBP and 47 weight % of 26B were applied. Such reaction mixture was obtained by the same reaction process described in Comparative Example 1, except the reaction time for the first and second reaction vessels was arranged to be 4 hours.

Later, the first vessel was heated at 180° C. with 0.3 MPa (gage pressure). The same crude material 26B as used in Comparative Example 1 was supplied at 127.5 g/hour. 6 weight % of potassium hydroxide solution was supplied at 3.2 g/hour, and the air was supplied at 10 NL/hour. Simultaneously, the second vessel was heated at 190° C. with 0.3 MPa (gage pressure), and the air was supplied at 2.5 NL/hour. Under such condition, the reaction was continuously carried out for 16 hours. Then, the reaction mixture flowing from the second vessel was analyzed by the chromatography. The result showed that TBBP within the reaction mixture was 65.7 weight % and the raw material 26B was 12.8 weight %. The selection ratio relative to 26B in the crude raw material 26B was 97.1%. In addition, Gardener dissolution color of 20 weight % of toluene solution in the reaction mixture was 14.

EXAMPLE 2

In this Example 2, the same condition as in the Example 1 was applied, except 6 weight % of potassium hydroxide solution was supplied at 2.2 g/hour in the first vessel and 1.0 g/hour in the second vessel. Later, the reaction mixture flowing from the second vessel was analyzed by the chromatography. The result showed that TBBP within the reaction mixture was 66.1 weight % and the raw material 26B was 12.2 weight %. The selection ratio relative to 26B in the crude raw material 26B was 96.9%. In addition, Gardener dissolution color of 20 weight % of toluene solution in the reaction mixture was 14.

EXAMPLE 3

In this Example 3, the same condition as in the Example 1 was applied for 16 hours, except 6 weight % of potassium hydroxide solution was supplied at 2.2 g/hour in the first vessel and 1.0 g/hour in the second vessel, and the air was supplied at 7.5 NL/hour in the first vessel and 5 NL/hour in the second vessel. Later, the reaction mixture flowing from the second vessel was analyzed by the chromatography. The result showed that TBBP within the reaction mixture was 65.1 weight % and the raw material 26B was 13.3 weight %. The selection ratio relative to 26B in the crude raw material 26B was 96.9%. In addition, Gardener dissolution color of 20 weight % of toluene solution in the reaction mixture was 15.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for continuously producing 3,3',5,5'-tetra-t-butyl-4,4'-biphenol by oxidizing/dimerizing 2,6-di-t-butylphenol, comprising the steps of:

supplying 2,6-di-t-butylphenol to a first reaction section of a reaction apparatus in which at least the first reaction section and a second reaction section are connected in series;

supplying alkali catalyst to at least said first reaction section; and distributing oxygen containing gas to each reaction section respectively;

whereby a reaction mixture containing 3,3',5,5'-tetra-t-butyl-4,4'-biphenol is obtained from a last reaction section.

2. The method as recited in claim 1, wherein the reaction apparatus comprises a first step reaction area including the first reaction section and a latter step reaction area including at least one reaction section, and reaction temperature in the latter step reaction area is higher than that in the first step reaction area.

3. The method as recited in claim 1, wherein said each reaction section is formed by independent reactors.

4. The method as recited in claim 1, wherein said each reaction section is formed by dividing an interior of a single reactor into plural sections.

5. The method as recited in claim 1, wherein the number of reaction sections in said reaction apparatus is from two to five.

6. The method as recited in claim 1, wherein the oxygen containing gas is continuously distributed to the first and second reaction sections and other subsequent reaction sections.

7. The method as recited in claim 1, wherein the oxygen containing gas is air.

8. The method as recited in claim 1, wherein 55–85% of the oxygen containing gas to be used is supplied to the first reaction section and the remaining volume of the gas is supplied to the second and its subsequent reaction section.

9. The method as recited in claim 1, wherein the alkali catalyst is continuously and separately supplied to each of the first and second reaction sections and other subsequent reaction sections.

10. The method as recited in claim 1, wherein more than 50% of the alkali catalyst to be used is supplied to the first reaction section and the remaining alkali catalyst is supplied to the second and other subsequent reaction sections.

11. The method as recited in claim 1, wherein the alkali catalyst is alkali metallic hydroxide.

12. The method as recited in claim 2, wherein the reaction temperature in the latter step reaction area is 170–200° C.

13. The method as recited in claim 2, wherein the reaction temperature in the latter step reaction area is higher by 0–30° C. than that of the first step reaction area.

* * * * *